United States Patent [19]

Hoelderich et al.

[11] Patent Number: 4,904,812
[45] Date of Patent: Feb. 27, 1990

[54] PREPARATION OF UNSATURATED NITRILES

[75] Inventors: Wolfgang Hoelderich, Frankenthal; Matthias Schwarzmann, Limburgerhof, both of Fed. Rep. of Germany

[73] Assignee: BASF Aktiengesellschaft, Ludwigshafen, Fed. Rep. of Germany

[21] Appl. No.: 281,915

[22] Filed: Dec. 7, 1988

Related U.S. Application Data

[63] Continuation of Ser. No. 107,997, Oct. 14, 1987, abandoned.

[30] Foreign Application Priority Data

Oct. 14, 1986 [DE] Fed. Rep. of Germany ........ 36914.3

[51] Int. Cl.$^4$ ............................................ C07C 120/00
[52] U.S. Cl. ...................................... 558/310; 558/462
[58] Field of Search ......................................... 558/310

[56] References Cited

U.S. PATENT DOCUMENTS

| | | | |
|---|---|---|---|
| 2,375,005 | 5/1945 | Kung | 558/310 |
| 3,043,860 | 7/1962 | Phillips et al. | 558/310 |
| 3,442,795 | 5/1969 | Kerr et al. | 208/120 |
| 3,560,550 | 2/1971 | Griswold et al. | 558/310 |
| 4,011,278 | 3/1977 | Plank et al. | 585/422 |

FOREIGN PATENT DOCUMENTS

| | | |
|---|---|---|
| 0196554 | 10/1986 | European Pat. Off. . |
| 0232712 | 8/1987 | European Pat. Off. . |
| 1256179 | 2/1961 | France . |
| 1397729 | 6/1975 | United Kingdom . |

OTHER PUBLICATIONS

"Ullmann's Encyclopedia of Industrial Chemistry", 5th Ed., Vol. A9, p. 578 [Date Unknown].
The Condensed Chemical Dictionary; 10th Ed. (1981), Hawley-Editor, pp. 1105–1106.
The Merck Index, 10th Ed. (1983), p. 1454, Listing No. 9922.
Chemistry & Industry; Rao et al., p. 270 (1984).

*Primary Examiner*—Joseph P. Brust
*Attorney, Agent, or Firm*—Keil & Weinkauf

[57] ABSTRACT

Unsaturated nitriles are prepared from lactones and NH$_3$ by a process in which the reaction of the lactone with NH$_3$ is carried in the presence of a zeolite as a catalyst.

A particularly suitable starting material is caprolactone and particularly suitable catalysts are zeolites of the pentasil type, for example aluminosilicate zeolites.

11 Claims, No Drawings

PREPARATION OF UNSATURATED NITRILES

This application is a continuation of application Ser. No. 107,997, filed on Oct. 14, 1987, now abandoned.

The present invention relates to a process for the preparation of unsaturated nitriles by cleaving lactones with ammonia in the presence of a zeolite as a catalyst.

It is known that nitriles can be prepared by thermal elimination of water from amides or carboxamides or their derivatives with ammonia in the presence of a suitable catalyst. Examples of catalysts used are alumina, silica, manganese oxide, thorium oxide and graphite catalysts. In order to achieve high conversions and yields, temperatures of 400°–500° C. are required. The known processes have the disadvantage that the catalysts are rapidly deactivated and lose their selectivity.

It is also known that lactones can be converted to hydroxycarboxamides in the presence of ammonia and the hydroxycarboxamides in turn can be readily and rapidly converted to the corresponding lactams with elimination of water.

The reaction of epsilon-caprolactone with ammonia in the gas phase over alumina gives 22% of hex-1-ene-6-nitrile and 24% of epsilon-hydroxycapronitrile.

In this reaction, from 70 to 80% of epsilon-hydroxycapronitrile are obtained when titanium dioxide is used as the catalyst, and from 50 to 73% of the said product when zinc oxide is used. Epsilon-hydroxycaproamide is also obtained using Ni-, Os-, Ir-, Rh- and Pt-containing hydrogenation and dehydrogenation catalysts, if necessary on a carrier such as $Al_2O_3$. If clay fragments impregnated with ammonium molybdate are used, lactones are converted to lactams and hydroxycarboxamides. Lactones and ammonia in the presence of hydrogen over alumina give hydroxycarbonitriles or aminoalkanols (U.S. Pat. No. 3,560,550).

U.S. Pat. No 2,375,005 discloses a two-stage process for the preparation of alpha, beta-unsaturated nitriles from lactones. In this process, the lactone is reacted with a large excess of $NH_3$ as a diluent or solvent in the presence of an alkali in a closed container under pressure to give a beta-hydroxycarboxamide. The reaction time required for this purpose is several hours. This amide is then reacted in a second stage over a dehydration catalyst such as $Al_2O_3$, $BaO_2$, $ThO_2$, $ZrO_2$ or $AlPO_4$.

It is an object of the present invention to cleave lactones with ammonia and convert them completely in one process step to the unsaturated nitriles, without the reaction stopping at the stage of the hydroxycarboxamides or hydroxycarbonitriles and without lactam formation. The catalysts used should have high activity and a long life.

We have found that this object is achieved and that the stated advantages in the preparation of unsaturated nitriles by catalytic cleavage of lactones with $NH_3$ are obtained if the reaction is carried out in the presence of a zeolite as a catalyst.

The reaction is advantageously carried out in the gas phase at from 150° to 500° C.

The novel process is based on a surprising effect and is noteworthy in that lactone cleavage to give unsaturated nitriles takes place in preference to lactam formation, which is also acid-catalyzed.

The novel process has the advantage that unsaturated nitriles are obtained from unsubstituted or alkyl-, aryl- or aralkyl-substituted 5-membered to 7-membered lactones in one stage.

Suitable lactones, methylbutyrolactones and valerolactones for the novel process are, for example, caprolactone, 7-methylcaprolactone, 6-ethylvalerolactone, 6-methylvalerolactone, 5-phenylbutyrolactone and 3,5-dimethylbutyrolactone. Caprolactone is the preferred starting material.

For example, in the case of caprolactone, the reaction according to the invention can be represented by the following equation:

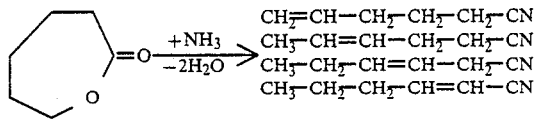

Zeolites, advantageously in the acidic form, are used as catalysts for the novel process. Zeolites are crystalline aluminum silicates, which have a highly ordered structure with a rigid three-dimensional network of $SiO_4$ and $AlO_4$ tetrahedra which are linked by common oxygen atoms. The ratio of Si and Al atoms to oxygen is 1:2. The electrovalency of the aluminum-containing tetrahedra is balanced by the inclusion of cations in the crystal, for example an alkali metal or hydrogen ion. Cation exchange is possible. The voids between the tetrahedra are occupied by water molecules before dehydration by drying or calcination.

In the zeolites, other elements, such as B, Ga, Fe, Cr, V, As, Sb, Bi or Be or mixtures of these, can be incorporated in the framework in place of aluminum, or the silicon can be replaced with a tetravalent element, such as Ge, Ti, Zr or Hf.

Zeolites are divided into various groups according to their structure. For example, the zeolite structure is formed by chains of tetrahedra in the mordenite group and by sheets of tetrahedra in the chabasite group, whereas in the faujasite group the tetrahedra are arranged to form polyhedra, for example in the form of a cubooctahedron which consists of four-membered rings and six-membered rings. Depending on the bonding of the cubooctahedra, resulting in cavities and pores of different sizes, a distinction is made between zeolites of type A, L, X and Y.

Catalysts which are suitable for the novel process are zeolites of the mordenite group and fine-pore zeolites of the erionite or chabasite type or zeolites of the faujasite type, for example, Y, X or L zeolites or zeolites of the ferrierite type.

This group of zeolites includes the ultrastable zeolites of the faujasite type, ie. dealuminated zeolites. Processes for the preparation of such zeolites have been described in many publications.

Particularly advantageous zeolites are those of the pentasil type. The common basic building block of these zeolites is a five-membered ring composed of $SiO_4$ tetrahedra. They have a high $SiO_2/Al_2O_3$ ratio and pore sizes which are between those of zeolites of type A and those of type X or Y.

These zeolites can have different chemical compositions. They are aluminosilicate, borosilicate, iron silicate, beryllium silicate, gallium silicate, chromium silicate, arsenic silicate, antimony silicate and bismuth silicate zeolites or mixtures of these, and aluminogermanate, borogermanate, gallium germanate and iron germanate zeolites or mixtures of these. The aluminosilicate, borosilicate and iron silicate zeolites of the pentasil type are particularly suitable for the novel process. The aluminosilicate zeolite is prepared, for example, from an aluminum compound, preferably Al(OH)$_3$ or Al$_2$(SO$_4$)$_3$, and a silicon component, preferably finely divided silica, in aqueous amine solution, in particular in polyamines, such as 1,6-hexanediamine or 1,3-propanediamine or triethylenetetramine solution, with or, in particular, without the addition of an alkali or alkaline earth, at from 100 to 220° C. under autogenous pressure. These include the isotactic zeolites according to European Patent 34,727 and 46,504. The aluminosilicate zeolites obtained have an SiO$_2$/Al$_2$O$_3$ ratio of from 10 to 40,000, depending on the choice of the amounts of starting materials. These aluminosilicate zeolites can be synthesized in an ether medium, such as diethylene glycol dimethyl ether, in an alcoholic medium, such as methanol or butane-1,4-diol, or in water Borosilicate zeolites can be synthesized, for example at from 90° to 200° C. under autogenous pressure by reacting a boron compound, eg. H$_3$BO$_3$, with a silicon compound, preferably finely divided silica, in aqueous amine solution, in particular in 1,6-hexanediamine or 1,3-propanediamine or triethylenetetramine solution with or, in particular, without the addition of an alkali or alkaline earth. These include the isotactic zeolites according to European Patents 34,727 and 46,504. Such borosilicate zeolites can also be prepared if the reaction is carried out in ether solution, eg. diethylene glycol dimethyl ether, or an alcoholic solution, eg. hexane-1,6-diol, instead of in aqueous amine solution.

The silicon-rich zeolites (SiO$_2$/Al$_2$O$_3$ $\geq$ 10) which can be used according to the invention also include the various ZSM types, NU-1 and Silicalit$^{(R)}$.

The iron silicate zeolite is obtained, for example, from an iron compound, preferably Fe$_2$(SO$_4$)$_3$, and a silicon compound, preferably finely divided silica, in aqueous amine solution, in particular 1,6-hexanediamine, with or without the addition of an alkali or alkaline earth, at from 100° to 200° C. under autogenous pressure.

The aluminosilicate, borosilicate and iron silicate zeolites prepared in this manner can be isolated, dried at from 100° to 160° C., preferably b 110° C., calcined at from 450° to 550° C., preferably 500° C., and then molded with a binder in a weight ratio of from 90:10 to 40:60 to give extrudates or pellets. Suitable binders are various aluminas, preferably boehmite, amorphous aluminosilicates having an SiO$_2$/Al$_2$O$_3$ ratio of from 25:75 to 90:5, preferably 75:25, silica, preferably finely divided SiO$_2$, mixtures of finely divided SiO$_2$ and finely divided Al$_2$O$_3$, TiO$_2$, ZrO$_2$ and clay. After the molding procedure, the extrudates or pellets are dried at 110° C. for 16 hours and calcined at 500° C. for 16 hours.

Advantageous catalysts are also obtained if the aluminosilicate or borosilicate zeolite isolated is molded directly after drying and is not subjected to calcination until after the molding procedure. The aluminosilicate and borosilicate zeolites prepared can be used in pure form, without a binder, as extrudates or pellets, examples of extrusion or peptizing assistants used being ethylcellulose, stearic acid, potato starch, formic acid, oxalic acid, acetic acid, nitric acid, ammonia, amines, silicoesters and graphite and mixtures of these.

If, because of its method of preparation, the zeolite is not in the catalytically active, acidic H form but, for example, in the Na form, the latter can be converted completely or partly to the desired H form by ion exchange, for example with ammonium ions, and subsequent calcination, or by treatment with an acid.

If, when the zeolite catalysts are used according to the invention, deactivation occurs as a result of coking, it is advisable to regenerate the zeolites by burning off the coke deposit with air or with an air/N$_2$ mixture at from 400° to 550° C., preferably 500° C. As a result, the zeolites regain their initial activity.

By means of precoking, it is possible to adjust the activity of the catalyst to give optimum selectivity with respect to the desired reaction product.

In order to obtain very high selectivity, high conversions and long catalyst lives, it is advantageous to modify the zeolites. In a suitable method of modifying the catalysts, for example, the unmolded or molded zeolites are doped with metal salts by ion exchange or impregnation. The metals used are alkali metals, such as Li, Cs or K, alkaline earth metals, such as Mg, Ca or Sr, metals of main groups 3, 4 and 5, such as Al, Ga, Ge, Sn, Pb or Bi, transition metals of subgroups 4-8, such as Ti, Zr, V, Nb, Cr, Mo, W, Mn, Re, Fe, Ru, Os, Co, Rh, Sr, Ni Pd or Pt, transition metals of subgroups 1 and 2, such as Cu, Ag or Zn, and rare earth metals, such as La, Ce, Pr, Nd, Er, Yb and U.

Doping is advantageously carried out as follows: the molded zeolite is initially taken in a riser tube, and an aqueous or ammoniacal solution of a halide or of a nitrate of the metals described above is passed over at from 20° to 100° C. Ion exchange of this type can be carried out on the hydrogen, ammonium and alkali metal forms of the zeolite. In another possible method of applying the metals to the zeolite, the zeolite material is impregnated, for example with a halide, a nitrate or an oxide of the metals described above in aqueous, alcoholic or ammoniacal solution. Both ion exchange and impregnation are followed at least by drying and, if desired, repeated calcination.

In a possible embodiment, for example, Cu(NO$_3$)$_2$.H$_2$O or Ni(NO$_3$)$_2$.6 H$_2$O or Ce(NO$_3$)$_3$6 H$_2$O or La(NO$_3$)$_2$6 H$_2$O or Cs$_2$CO$_3$ is dissolved in water, and this solution is used to impregnate the molded or unmolded zeolite for a certain time, for example 30 minutes. Any supernatant solution is freed from water in a rotary evaporator. Thereafter, the impregnated zeolite is dried at about 150° C. and calcined at about 550° C. This impregnation process can be carried out several times in succession in order to obtain the desired metal content.

It is also possible to prepare an aqueous Ni(NO$_3$)$_2$ solution or ammoniacal Pd(NO$_3$)$_2$ solution and to suspend the pure zeolite powder therein at from 40° to 100° C. for about 24 hours, while stirring. After it has been filtered off, dried at about 150° C. and calcined at about 500° C., the zeolite material thus obtained can be further processed with or without a binder to give extrudates, pellets or fluidizable material.

The zeolite in the H form, ammonium form or alkali metal form can be subjected to ion exchange by a method in which the zeolite, in the form of extrudates or pellets, is initially taken in a column, and, for example, an aqueous Ni(NO$_3$)$_2$ solution or ammoniacal Pd(NO$_3$)$_2$ solution is circulated over the said zeolite at slightly elevated temperatures of from 30° to 80° C. for from 15 to 20 hours. The product is then washed thoroughly with water, dried at about 150° C. and calcined at about 550° C. In the case of some metal-doped zeolites, for example Pd-, Cu- and Ni-doped zeolites, aftertreatment with hydrogen is advantageous.

In another possible method of modification, the molded or unmolded zeolite material is treated with an acid, such as hydrochloric acid, hydrofluoric acid or phosphoric acid, and/or steam. In an advantageous procedure for this purpose, for example, the zeolite in powder form is treated with 1 N phosphoric acid for 1 hour at 80° C. After the treatment, the product is washed with water, dried at 110° C. for 16 hours and calcined at 500° C. for 20 hours. In another procedure, zeolites, before or after they have been molded with a binder, are treated with a 3–25, in particular 12–20, % strength by weight aqueous hydrochloric acid, for example for from 1 to 3 hours at from 60° to 80° C. The zeolite treated in this manner is then washed with water, dried, and calcined at from 400° to 500° C.

In a particular embodiment of the acid treatment, the zeolite material, before being premolded, is treated at elevated temperatures with hydrofluoric acid, which is generally used in the form of from 0.001 N to 2 N, preferably from 0.05 N to 0.5 N, hydrofluoric acid, for example by refluxing for, in general, from 0.5 to 5, preferably from 1 to 3, hours. After the zeolite material has been isolated, for example by filtering it off and washing it thoroughly, it is advantageously dried at, for example, from 100° to 160° C. and calcined at, in general, from 450° to 600° C. In another preferred embodiment of the acid treatment, the zeolite material is molded with a binder and then treated at elevated temperatures, advantageously at from 50° to 90° C., preferably from 60° to 80° C., for from 0.5 to 5 hours, preferably with 12–20% strength by weight hydrochloric acid. The zeolite material is advantageously then washed thoroughly, dried at from 100° to 160° C. and calcined at from 450° to 600° C. An HF treatment can also be followed by an HCL treatment.

In another procedure, zeolites can be modified by applying phosphorus compounds, such as trimethoxy phosphate, trimethoxyphosphine or primary, secondary or tertiary sodium phosphate. The treatment with primary sodium phosphate has proven particularly advantageous. In this procedure, the zeolites in the form of extrudates, pellets or fluidizable material are impregnated with aqueous $NaH_2PO_4$ solution, dried at 110° C. and calcined at 500° C.

The catalysts described here can alternatively be used as 2–4 mm extrudates, as pellets having a diameter of 3–5 mm, as chips having particle sizes of 0.1–0.5 mm or as a fluidizable catalyst.

The molar ratio of lactones to $NH_3$ is advantageously from 1:1 to 1:30, in particular from 1:3 to 1:10. Larger amounts of ammonia are possible but uneconomical. The ammonia can be added in gaseous form or as an aqueous solution.

The reaction is advantageously carried out in the gas phase, in general at from 100° to 500° C., advantageously from 200° to 450° C., in particular from 250° to 400° C., as a rule under from 0.1 to 100, in particular from 0.5 to 10, bar. In the reaction in the gas phase, a space velocity of from 0.1 to 20, in particular from 1 to 10, g of lactone per g of catalyst per hour is advantageously maintained.

The reaction may be effected in a fixed bed or fluidized bed. However, it is also possible to carry out the reaction in the liquid phase (suspension, trickle-bed or liquid phase procedure) at from 50° to 220° C., batchwise or, preferably, continuously.

Sparingly volatile or solid starting materials can be used in dissolved form, for example in solution in tetrahydrofuran, toluene or petroleum ether. In general, the starting materials may be diluted with a solvent or an inert gas, such as $N_2$, Ar or steam.

After the reaction, the products formed are isolated from the reaction mixture by a conventional method, for example by distillation; unconverted starting mixture is, if desired, recycled to the reaction.

The unsaturated nitriles obtained by the novel process are versatile intermediates. They are useful, for example, for the preparation of fiber intermediates, crop protection agents and drugs.

EXAMPLES 1 TO 8

The reaction is carried out in the gas phase under isothermal conditions in a tube reactor (coil, 0.6 cm internal diameter, 90 cm length) in the course of not less than 6 hours. The reaction product is isolated and determined by conventional methods. Quantitative determination of the reaction products and of the unconverted starting materials is carried out by gas chromatography.

The catalysts used for the examples are:

Catalyst A

A borosilicate zeolite of the pentasil type is prepared by hydrothermal synthesis from 640 g of finely divided $SiO_2$, 122 g of $H_3BO_3$ and 8000 g of an aqueous 1,6-hexanediamine solution (weight ratio 50:50) at 170° C. under autogenous pressure in a stirred autoclave. The crystalline reaction product is filtered off, washed thoroughly, dried at 100° C. for 24 hours and calcined at 500° C. for 24 hours. This borosilicate zeolite is composed of 94.2% by weight of $SiO_2$ and 2.3% by weight of $B_2O_3$.

This material is molded with a molding assistant to prepare 2 mm extrudates, which are dried at 110° C. for 16 hours and calcined at 500° C. for 24 hours.

Catalyst B

An aluminosilicate zeolite of the pentasil type is prepared under hydrothermal conditions, under autogenous pressure and at 150° C., from 65 g of finely divided $SiO_2$ and 20.3 g of $Al_2(SO_4)_3 \cdot 18\,H_2O$ in 1 kg of an aqueous 1,6-hexanediamine solution (weight ratio 50:50) in a stirred autoclave. The crystalline reaction product is filtered off, washed thoroughly, dried at 110° C. for 24 hours and calcined at 500° C. for 24 hours. This aluminosilicate zeolite contains 91.6% by weight of $SiO_2$ and 4.6% by weight of $Al_2O_3$. The zeolite is molded with boehmite in a weight ratio of 60:40 to give 2 mm extrudates, which are dried at 110° C. for 16 hours and calcined at 500° C. for 24 hours.

Catalyst C

Catalyst C is obtained by impregnating catalyst B with an aqueous $Cr(NO_3)_3$ solution. The impregnated extrudates are dried at 130° C. for 2 hours and calcined at 540° C. for 2 hours. The Cr content is 2.3% by weight.

Catalyst D

A commercial NaY zeolite is extruded with boehmite in a weight ratio of 60:40, dried at 100° C. and calcined at 500° C. for 16 hours, after which it is subjected to ion exchange with 20% strength ammonium chloride solution. The residual sodium content of catalyst D is 0.2% by weight (calcined at 500° C.).

Catalyst E

Commercial ferrierite (Zeolon 700 ®) is molded with boehmite in a weight ratio of 60:40 to give 2 mm extrudates, which are then dried at 110° C. and calcined at 500° C. for 16 hours. These extrudates are subjected to ion exchange with 20% strength ammonium chloride solution until the residual sodium content of catalyst E is 0.85% by weight (calcined at 500° C. for 5 hours).

Catalyst F

Borosilicate zeolite described under catalyst A, molded with boehmite in a weight ratio of 60:40 to give 2 mm extrudates, dried at 110° C. for 16 hours and calcined at 500° C. for 24 hours.

Catalyst G 100 g of the borosilicate zeolite used as catalyst A are treated with 280 ml of 0.1 N HF at 90° C. for 2 hours, filtered off and then dried at 160° C. This product is molded with an amorphous aluminosilicate (25% by weight $Al_2O_3$ and 75% by weight $SiO_2$) in a weight ratio of 60:40 to give 2 mm extrudates, which are dried at 110° C. for 16 hours and calcined at 500° C. for 16 hours.

The experimental results obtained with these catalysts, and the reaction conditions, are summarized in Table 1.

TABLE 1

| | Caprolactone (I) + $NH_3$ → hexenenitriles | | | | |
|---|---|---|---|---|---|
| Example | 1(1) | 2(1) | 3(1) | 4(2) | 5(2) |
| Catalyst | A | B | C | D | E |
| Temperature | 400° C. | 400° C. | 400° C. | 400° C. | 400° C. |
| WHSV | 2.1 $h^{-1}$ | 2.6 $h^{-1}$ | 2.6 $h^{-1}$ | 4.5 $h^{-1}$ | 4.5 $h^{-1}$ |
| Molar ratio I:$NH_3$ | 1:7 | 1:7 | 1:7 | 1:1.6 | 1:1.6 |
| Conversion % | 100 | 100 | 100 | 99 | 100 |
| Selectivity % | | | | | |
| Hexenenitriles | 86.1 | 81.5 | 85.7 | 75.0 | 75.2 |

(1)$NH_3$ in the form of a 25% strength aqueous solution is mixed with caprolactone
(2)$NH_3$ is introduced in gaseous form, separately from caprolactone Byproducts of the reaction are hexane, hexadienenitriles, hydroxycapronitrile, hexenamide and a small amount of caprolactam.

TABLE 2

| | gamma-valerolactone (I) + $NH_3$ → butenenitriles | | |
|---|---|---|---|
| Examples | 6 | 7 | 8 |
| Catalyst | F | B | G |
| Temperature | 400 ° C. | 400° C. | 400° C. |
| WHSV | 3.5 $h^{-1}$ | 3.5 $h^{-1}$ | 3.5 $h^{-1}$ |
| I:$NH_3$ | 1:3 | 1:3 | 1:3 |
| Conversion % | 74.7 | 90.9 | 81.7 |
| Selectivity % | | | |

TABLE 2-continued

| | gamma-valerolactone (I) + $NH_3$ → butenenitriles | | |
|---|---|---|---|
| Examples | 6 | 7 | 8 |
| Butenenitriles | 85.0 | 91.6 | 83.5 |

We claim:
1. A process for preparing olefinically unsaturated nitriles which comprises: in one process step, cleaving lactones, containing 5 to 7 ring members and being unsubstituted or alkyl-, aryl- or aralkyl substituted by reacting the lactone with ammonia at a temperature of 150°–500° C. and in a molar ratio of lactone to ammonia of from 1:1 to 1:30 in the presence of a zeolite catalyst.
2. The process of claim 1, wherein the lactone is caprolactone.
3. The process of claim 1, wherein the catalyst used is a pentasil zeolite.
4. The process of claim 1, wherein the catalyst used is a faujasite aluminosilicate zeolite.
5. The process of claim 1, wherein the catalyst used is an erionite or chabazite aluminosilicate zeolite.
6. The process of claim 1, wherein the catalyst used is a ferrierite aluminosilicate zeolite.
7. The process of claim 1 wherein the catalyst used is a zeolite doped with an alkali metal, an alkaline earth metal, a transition metal, a rare earth or mixture thereof.
8. The process claim 1, wherein the reaction is carried out in the gas phase, the lactone is caprolactone, the zeolite is pentasil zeolite and the reaction temperature is from 150° to 500° C.
9. The process of claim 1, wherein the lactone is selected from the group consisting of caprolactone, 7-methylcaprolactone, 6-ethylvalerolactone, 6-methylvalerolactone, 5-phenylbutyrolactone and 3,5-dimethylcaprolactone.
10. A process for preparing olefinically unsaturated nitriles which comprises: in one process step, cleaving lactones, containing 5 to 7 ring members and being unsubstituted or alkyl-, aryl- or aralkyl- substituted by reacting the lactone with ammonia at a temperature of 150°–500° C. and in a molar ratio of lactone to ammonia of from 1:1 to 1:30 in the presence of a borosilicate, iron silicate, beryllium silicate, gallium silicate, chromium silicate, arsenic silicate, antimony silicate, bismuth silicate, aluminogermanate, borogermanate, gallium germanate or iron germanate zeolite catalyst or mixtures thereof.
11. A process as defined in claim 9 wherein the zeolite catalyst is a borosilicate or iron silicate pentasil zeolite.

* * * * *